United States Patent [19]

Orzalesi

[11] 4,388,325

[45] Jun. 14, 1983

[54] L-ARGININE D,L-PYROGLUTAMATE AS A PHARMACEUTICAL AGENT HAVING AN ACTIVITY AT THE NEURO-ENDOCRINAL LEVEL

[75] Inventor: Giovanni Orzalesi, Florence, Italy

[73] Assignee: Societa' Italo-Britannica L. Manetti-H. Roberts & C., Florence, Italy

[21] Appl. No.: 275,774

[22] Filed: Jun. 22, 1981

[30] Foreign Application Priority Data

Jun. 30, 1980 [IT] Italy ............................. 49111 A/80

[51] Int. Cl.$^3$ .................... A01N 37/12; A61K 31/195
[52] U.S. Cl. .................................................. 424/319
[58] Field of Search ........................................ 424/319

[56] References Cited

PUBLICATIONS

Chemical Abstracts, vol. 83, (1975), Pars. 202,005e.

Primary Examiner—Elbert L. Roberts

[57] ABSTRACT

L-arginine D,L-pyroglutamate has a tonic activity at the neuro-endocrinal level with a specific effect in enhancing sexual behavior of Mammalia males, particularly in individuals of elderly age, humans being included. To be used in the pharmaceutical and veterinary field.

3 Claims, No Drawings

L-ARGININE D,L-PYROGLUTAMATE AS A PHARMACEUTICAL AGENT HAVING AN ACTIVITY AT THE NEURO-ENDOCRINAL LEVEL

This invention relates to a new pharmaceutical use for L-arginine D,L-pyroglutamate based on the tonic neuroendocrinal activity thereof, which leads to a more active sexual behaviour, in male subjects of the Mammalia class, including humans.

L-arginine D,L-pyroglutamate is a well defined chemical compound which can be obtained by an equimolecular combination of D,L-pyroglutamic acid and L-arginine as described in British Pat. No. 1,421,089 included herein by reference.

The specific activity of L-arginine D,L-pyroglutamate on the central nervous system which results in a stimulating effect of the brain, is known from Italian patent application No. 52256A/78. With respect to this activity, the evidence that the drug molecule passes, unmodified, through and beyond the hematocephalic barrier is of particular significance.

The object of the present invention is a new pharmaceutical use of L-arginine D,L-pyroglutamate for treatment of deficient sexual behavior, particularly in aged subjects. It has been found that L'-arginine D,L-pyroglutamate acts on the central nervous system, presumably at the neuroendocrinal level, in cases of dopaminergic tone deficiency. Indeed it has been found that this activity results in a more active response to various conditioned situations, including the sexual stimulation of males.

Consequently, the object of the present invention is the use of an active agent based on L-arginine D,L-pyroglutamate, as well as pharmaceutical compositions containing it, in treatment of sexually deficient behavior in humans.

A further object of the present invention is the use of said active agent to stimulate sexual activity in animals of the Mammalia class.

The therapeutical activity of L-arginine D,L-pyroglutamate has been tested on rats as well as on male human volunteers to determine the increase of sexual activity.

The techniques followed in the experimental tests will be described hereinafter and are exemplary only and non-limiting, said techniques allowing a complete reproducibility of the results.

Rats have been tested using the so-called "pole jumping" test for determining the effect of L-arginine D,L-pyroglutamate on the "conditioned avoidance response". Sexual behaviour tests were also carried out on the same types of rat and the results indicate that L-arginine D,L-pyroglutamate acts by improving specific dopaminergic tone. Experimental tests were then carried out on humans which confirmed the test results on rats as to the activity of the compound of this invention.

The above tests are described in detail below.

METHODS AND MATERIALS

Wistar male rats were employed. The first group was of an age of about 3 months weighing $150\pm10$ g (young rats), the second group was more than 16 months old weighing $430\pm20$ g (old rats). Additionally CDR rats weighing $190\pm10$ g were employed.

The animals were housed in a thermally regulated cabin programmed with a dark-light cycle (light from 8.00 p.m. to 8.00 a.m., and dark from 8.00 a.m. to 8.00 p.m.) with food and water ad libitum. The rats were divided into lots of 10 and treated for 15 days according to the following schedule which was the same for all rats (young, old and CDR): L-arginine D,L-pyroglutamate 100 mg/kg pro die, intraperitoneally; L-arginine D,L-pyroglutamate 1000 mg/kg pro die, i.p.; physiologic solution, isovolumetric dose, i.p. After this treatment the animals were subjected to the pole jumping behaviour test.

POLE JUMPING TEST IN MALE RATS

This test was used to determine the conditioned avoidance response of rats treated with the compound of the invention in comparison with untreated rats. The animals had to jump upon a pole placed vertically at the center of a box having transparent walls in order to avoid an electric shock transmitted through an electrified network forming the bottom of the box. The electric shock was set at 0.25 mA.

The conditioning stimulation (CS) was produced by switching on a 40 watt lamp fixed above the box. The CS was effected 5 seconds before the beginning of the unconditional stimulation (US) provided by the electric shock. As soon as the animal jumped upon the pole, both CS and US ceased. Each time the animal jumped in response to CS only, this constitutes a "conditioned avoidance response" (CAR); the light was immediately switched off and the US was not fed.

For three consecutive days (learning period) 10 stimulations were provided daily with an average interval between stimulations of 60 seconds. On the fourth day of test the US was no longer provided (extinction period); on the same fourth day such a test was repeated twice, with an interval of two hours. A fourth extinction test was carried out on the fifth day.

The pole jumping test was started on the tenth day of treatment with the compound of the invention (the end of treatment was coincident with the fifth day of test). The results of the pole jumping test are listed in Table 1, wherein significant levels of average values for the different lots of rats have been calculated by t according to the Student method. In Table 1 a higher figure indicates a more rapid average response and a lower figure indicates a less rapid average response.

TABLE 1

| | Activity of L-arginine D,L-pyroglutamate in the pole jumping test (CAR) | | | | | | |
|---|---|---|---|---|---|---|---|
| | Learning period | | | Extinction period | | | |
| Treatment | 1st day | 2nd day | 3rd day | 4th day A | 4th day B | 4th day C | 5th day |
| Young rats: | | | | | | | |
| PCA 100 mg/kg | $1.5 \pm 0.6$ | $6.3 \pm 0.4$ | $8.2 \pm 0.2$ | $8.3 \pm 0.8$ | $8.5 \pm 0.8^{++}$ | $7.0 \pm 0.6^{++}$ | $5.0 \pm 0.3$ |
| PCA 1000 mg/kg | $1.7 \pm 0.6$ | $5.9 \pm 0.4$ | $8.1 \pm 0.5$ | $8.1 \pm 0.4$ | $7.2 \pm 0.4^{++}$ | $5.2 \pm 0.8^{++}$ | $3.2 \pm 0.6$ |
| physiologic solution | $1.4 \pm 0.5$ | $6.4 \pm 0.5$ | $7.6 \pm 0.4$ | $8.2 \pm 0.3$ | $2.1 \pm 0.3$ | $1.2 \pm 0.4$ | $0.3 \pm 0.3$ |
| Old rats: | | | | | | | |
| PCA 100 mg/kg | $1.4 \pm 0.3$ | $6.3 \pm 0.4^{+}$ | $8.4 \pm 0.3^{+}$ | $8.3 \pm 0.3^{+}$ | $8.1 \pm 0.3^{++}$ | $6.3 \pm 0.8^{++}$ | $4.4 \pm 0.8$ |
| PCA 1000 mg/kg | $1.4 \pm 0.2$ | $5.8 \pm 0.6^{+}$ | $7.5 \pm 0.5^{+}$ | $7.3 \pm 0.1^{+}$ | $7.1 \pm 0.8^{++}$ | $4.9 \pm 0.9^{++}$ | $3.7 \pm 0.6$ |

TABLE 1-continued

| | Activity of L-arginine D,L-pyroglutamate in the pole jumping test (CAR) | | | | | | |
|---|---|---|---|---|---|---|---|
| | Learning period | | | Extinction period | | | |
| Treatment | 1st day | 2nd day | 3rd day | 4th day A | 4th day B | 4th day C | 5th day |
| physiologic solution CDR rats: | 1.3 ± 0.1 | 4.1 ± 0.6 | 4.2 ± 0.8 | 4.9 ± 0.3 | 2.9 ± 0.4 | 1.0 ± 0.3 | 0.1 ± 0.4 |
| PCA 100 mg/kg | 1.4 ± 0.3 | 5.3 ± 0.7+ | 7.4 ± 0.7+ | 8.1 ± 0.5++ | 8.0 ± 0.2++ | 6.8 ± 0.4++ | 3.2 ± 0.2 |
| PCA 1000 mg/kg | 1.3 ± 0.1 | 5.1 ± 0.6+ | 7.4 ± 0.6+ | 7.3 ± 0.6+ | 6.9 ± 0.2++ | 3.9 ± 0.3++ | 3.1 ± 0.4 |
| physiologic solution | 1.3 ± 0.1 | 2.5 ± 0.2 | 3.5 ± 0.3 | 3.4 ± 0.7 | 1.2 ± 0.2 | 0.4 ± 0.0 | 0.2 ± 0.2 |

+$p < 0.05$ versus controls
++$p < 0.01$ versus controls

RESULTS

It can be seen from Table 1, that in the learning period the figures relative to the old rats and untreated CDR rats are significantly lower than the figures relative to rats treated with the compound of the invention, while no significative improvement is observed in the treated young rats with respect to untreated young rats.

In the extinction period each lot of treated animals shows figures which are significantly higher than the untreated lots.

SEXUAL BEHAVIOR TEST

Male Wistar rats were employed weighing 220±10 g. These rates were divided into lots labeled as slow copulators and normal copulators. In selecting these lots each rat was preliminarily subjected to 5 tests with a female in estrus at a week's interval.

Animals with less than two ejaculations and a latent period at the first ejaculation higher than 15 minutes were allotted to the slow copulator lot, while animals with two or more ejaculations and a latent period at the first ejaculation lower than 15 minutes were allotted to the normal copulator lot. Female Wistar rats were ovaryectomized three weeks before beginning the test and were brought into estrus by subcutaneous injection of extradiol and progesterone.

Slow and normal copulator males were treated according to the following schedule which was identical for both groups:
L-arginine D,L-pyroglutamate, 1000 mg/kg i.p.
physiological solution, isovolumetric dose, i.p.

Each behavior test was carried out from 5.00 p.m. to 7.00 p.m. with a period of darkness. One female was introduced into the cage of each male and the test was stopped after an observation of 30 minutes. The following parameters were determined: latent period to first mounting, to first intromission and to first ejaculation; interval between intromissions and after ejaculation; frequency of mounting, intromission and ejaculation.

The sexual behavior test was carried out at the end of a 15 day treatment with the compound according to the invention.

The levels of significance between the average values of the various parameters have been calculated according to t of the Student method.

The results are listed in Table 2.

TABLE 2

| | Activity of L-arginine D,L-pyroglutamate on sexual behavior in rats | | | |
|---|---|---|---|---|
| | Normal copulators | | Slow copulators | |
| Parameters | PCA 1000 mg/kg | physiologic solution | PCA 1000 mg/kg | physiologic solution |
| Latent period: | | | | |
| Mounting | 98.2 ± 13.7 | 95.4 ± 12.1 | 86.2 ± 32.2 | 92.1 ± 23.9 |
| Intromission | 129.7 ± 17.7 | 123.1 ± 11.9 | 110.4 ± 25.0+ | 165.6 ± 11.4 |
| Ejaculation | 558.5 ± 87.9 | 574.1 ± 84.2 | 683.7 ± 91.0++ | 976.4 ± 87.9 |
| Intervals: | | | | |
| Post-ejaculation | 317.1 ± 21.8 | 327.8 ± 32.4 | 389.0 ± 15.5++ | 571.8 ± 84.9 |
| Inter-intromission | 52.2 ± 9.1 | 59.8 ± 12.9 | 59.9 ± 11.6+ | 79.4 ± 41.3 |
| Frequency: | | | | |
| Mounting | 4.4 ± 1.2 | 4.1 ± 0.7 | 4.0 ± 1.0+ | 2.8 ± 0.9 |
| Intromission | 16.4 ± 1.8 | 11.6 ± 1.1 | 13.9 ± 2.0++ | 6.8 ± 0.3 |
| Ejaculation | 2.1 ± 0.7 | 2.1 ± 0.8 | 2.4 ± 0.7+ | 1.2 ± 0.0 |

+$p < 0.05$ versus controls
++$p < 0.01$ versus controls
Measures are expressed in seconds.

RESULTS OF THE SEXUAL BEHAVIOR TEST

Table 2 indicates that the sexual behavior of treated normal copulator rats is not modified compared to untreated normal copulator rats. On the contrary slow copulator rats treated by the compound of the invention show a significative increase in sexual activity compared to untreated slow copulator rats.

The following is a comment on the results of the previously mentioned tests.

The deficit of learning capability and the more rapid extinction time in the pole jumping test are connected, at least in some part, to the well known deficiency of dopaminergic tone which is present in CDR animals as well as in normal aging animals.

Sexual behavior is, as it is well known, a dopamine mediated behavior. In individuals having deficient copulating behavior, a deficiency of central dopaminergic tone exists. As indicated by the pole jumping test on CDR and old individuals, the activity on sexual behavior caused by the compound of the present invention can be explained by an improvement of the specific dopaminergic tone.

SEXUAL BEHAVIOR TEST IN HUMANS

Based on the results obtained with animals as well as the fact that L-arginine D,L-pyroglutamate is a drug having no toxic effect, i.e. which does not show any significative collateral effect, even at very high dosage for an extended period of time, a clinical experimentation was carried out on male human volunteers in order to determine if the compound of the invention can increase the sexual tone in humans as it did in rats.

It was assumed that subjects less than 40 years old had to be considered as normal copulators, while subjects more than 60 years old should better represent statistically a lot of slow copulators. In both cases care was taken to subject married individuals to the treatment or individuals which in some way could have a normal access to sexual activity.

As to the pharmaceutical form, in a purely exemplary and non-limiting, operculated capsules containing a dose of 250 mg of active substance were used.

Forms were prepared instructing the subjects of both lots to record the frequency data of their sexual activity during three months before the treatment with L-arginine D,L-pyroglutamate and administering them placebo capsules during that time, as if the treatment was already underway and should last for 6 months. In no case were the female partners advised that any experiment was in the process of being carried out.

The treatment consisted of oral administration of 1000-1500-2000 mg pro die of L-arginina D,L-pyroglutamate for the subsequent three months. Both lots (normal copulators and slow copulators) were represented by 35 individuals for each of the three dosages. The results are listed in Table 3 wherein the data indicates the number of sexual intercourses which occurred in each lot.

recovery of the frequency of sexual intercourse and such a recovery increased in proportion with the administered dosage.

From the tests carried out and from a comprehensive evaluation of results yielded thereby, it can be asserted that L-arginine D,L-pyroglutamate is a drug which can be directed to a new clinical utilisation in view of the clear and surprising activity thereof, on a neuroendocrinal basis (via hypothalamus) for increasing the dopaminergic tone in favour of sexual performance of male subjects. These male subjects being about 60 years in age or sexually scarcely active for various reasons, but in ages lower than the above limit.

A similar utilization can be found, if needed, in reproduction of animals of the Mammalia class at a dose level proportioned to the mg/kg body weight ratio.

In view of its very high tolerability, L-arginine D,L-pyroglutamate can be administered orally or parenterally at high dosages.

Dosages per os for the above mentioned utilization can be of 200 to 4500 mg per day and preferably from 500 to 2500 mg per day. Parenterally the dosages can preferably be from 200 to 1200 mg per day or more.

The following are examples of preparations suitable for administration:

Oral vials:

| | |
|---|---|
| L-Arginine D,L-pyroglutamate | 500 mg |
| Excipients (Para-combin) | 25 mg |
| Tetraroma Orange | 2 mg |
| Sugar syrup 70% to | 5 ml |

TABLE 3

Activity of L-arginine D,L-pyroglutamate on sexual behavior of male humans in clinical tests

| Month | Under forty years | | | Over sixty years | | |
|---|---|---|---|---|---|---|
| I | 490 | 511 | 465 | 153 | 165 | 181 |
| II | 475 | 520 | 480 | 160 | 182 | 175 |
| III | 483 | 525 | 561 | 159 | 190 | 188 |
| Dosage: | 1000++ | 1500++ | 2000++ | 1000++ | 1500++ | 2000++ |
| IV | 526 | 583 | 605 | 280 | 291 | 330 |
| V | 540 | 560 | 634 | 356 | 318 | 385 |
| VI | 581 | 591 | 648 | 389 | 420 | 493 |

The data represent the number of sexual intercourses in each lot.
+Both lots included 35 individuals for each of the three dosages.
++Dosage of L-arginine D,L-pyroglutamate in mg pro die, per os.
Placebo during the first three months.

The statistical analysis of the test results reported in Table 3 is illustrated in Table 4 hereinbelow.

TABLE 4

Statistical analysis of clinical results of L-arginine D,L-pyroglutamate on sexual activity

| Dosage (mg/die) per os | Treatment period (months) | Under forty years | | | | Over sixty years | | | |
|---|---|---|---|---|---|---|---|---|---|
| | | Average of controls | Average of treated individuals | T | P | Average of controls | Average of treated individuals | T | P |
| 1000 | 1 | 13.69 | 14.63 | 0.966 | >0.05 | 4.40 | 7.74 | 4.954 | <0.01 |
| 1000 | 2 | 13.57 | 15.06 | 1.405 | >0.05 | 4.54 | 10.17 | 9.985 | <0.01 |
| 1000 | 3 | 13.80 | 16.57 | 3.582 | <0.01 | 4.54 | 10.89 | 9.025 | <0.01 |
| 1500 | 1 | 14.89 | 16.37 | 1.570 | >0.05 | 4.71 | 7.49 | 3.363 | <0.01 |
| 1500 | 2 | 14.86 | 15.69 | 0.868 | >0.05 | 5.14 | 8.83 | 6.121 | <0.01 |
| 1500 | 3 | 14.60 | 16.40 | 2.002 | >0.05 | 5.14 | 12.00 | 9.559 | <0.01 |
| 2000 | 1 | 13.29 | 17.28 | 4.570 | <0.01 | 5.00 | 9.14 | 6.549 | <0.01 |
| 2000 | 2 | 13.71 | 18.11 | 5.059 | <0.01 | 4.86 | 10.66 | 4.431 | <0.01 |
| 2000 | 3 | 16.03 | 18.51 | 2.775 | <0.01 | 5.29 | 13.83 | 12.402 | <0.01 |

The experimental results show that while in normal copulator subjects noticeable variations cannot be observed between the non-treatment period (1st to 3rd month) and the treatment period (4th to 6th month), in slow copulator subjects the treatment led to a clear Operculated capsules:

| | |
|---|---|
| L-Arginine D,L-pyroglutamate | 250 mg |

-continued

| Excipients (starch sta-RX-150) | 98 mg |
|---|---|
| Magnesium stearate | 2 mg |

Parenteral vials:

| L-arginine D,L-pyroglutamate | 100 mg |
|---|---|
| Sterile bidistilled water to | 5 ml |
| or: | |
| L-arginine D,L-pyroglutamate | 300 mg |
| Sterile bidistilled water to | 10 ml |

I claim:

1. A method for increasing on a neuro-endocrinal basis sexual activity in male mammals, said sexual activity of which has decreased or become deficient due to specific dopaminergic hypotonicity, comprising administering to said mammals an amount of L-arginine D,L-pyroglutamate effective to increase said sexual activity.

2. The method of claim 1, wherein said L-arginine D,L-pyroglutamate is administered orally at a daily dosage of from 200 to 4500 mg.

3. The method of claim 1, wherein said L-arginine D,L-pyroglutamate is administered parenterally at a daily dosage from 200 to 1200 mg.

* * * * *